US00PP09557P

United States Patent [19]

Suzuki et al.

[11] Patent Number: Plant 9,557

[45] Date of Patent: May 21, 1996

[54] PETUNIA PLANT 'SUNTORY SP-R'

[75] Inventors: Kenichi Suzuki, Ibaraki; Yoshiji Nishikawa, Yamanashi; Yasuyuki Murakami, Kofu, all of Japan

[73] Assignee: Suntory Limited, Osaka, Japan

[21] Appl. No.: 415,304

[22] Filed: Apr. 3, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Burns, Doane, Swecker & Mathis

[57] ABSTRACT

Disclosed herein is a petunia plant having a intermediate habit type between upright habit type and decumbent habit type. The plant has abundant branching and a great profusion of blooms, and the whole bush remains in bloom for a long period of time. The flowers are single and very small, and the petals have a vivid reddish purple color and vivid greenish yellow throat inside portion. The plant is highly resistant to cold, rain, heat, and disease.

4 Drawing Sheets

BACKGROUND OF THE VARIETY

The present invention relates to a new and distinct variety of petunia plant obtained from crossing one petunia plant "P105" (♀) having reddish purple petal which was selected from a crossing of a wild type of petunia plant native to Brazil, and one petunia plant "P107" (♂) having reddish purple petal (but, different from the female parent) which was selected from a crossing of a wild type of petunia plant native to Brazil.

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e., the 'Revolution' series [('Revolution Purplepink' (U.S. Plant Pat. No. 6,195), 'Revolution Brilliantpink' (U.S. Plant Pat. No. 6,914), and 'Revolution Brilliantpink-mini' (U.S. Plant Pat. No. 6,899)] is a decumbent type plant having long stems, a lower plant height, abundant branching, and a high resistance to heat, cold and rain. However, there are only a few varieties having a great profusion of flowers with a very small flower diameter, and a high resistance to rain, heat, cold, and diseases. Accordingly, this invention was aimed at obtaining a new variety having a vivid reddish purple color petal, together with the above features.

Four plants of a few wild types of petunia plants from Brazil, having flowers with a small flower diameter were selected, in view of plant form, flower color, and flower bloom. The selected plants were propagated in Janurary, 1990 at the Plant Biotechnology Laboratory, Institute for Fundamental Research of SUNTORY Ltd., residing at 2913-1 Torihara, Hakushu-cho, Kitakoma-gun, Yamanashi-ken, Japan, interspecies crossing of flowering plants was begun from May, 1990, and then, by January, 1991, 300 interspecies crossing plants were obtained. 12 plants were selected from this crossing, propagated by interstock crossing, and 1000 plants were obtained in January, 1992. From these, 20 plants were selected by pot trial. The selected 20 plants were propagated by cutting, and then grown in bed and pot on trial from May, 1992. Finally only one of the 20 plants was selected. The botanical characteristics of the finally-selected plant were than examined, using a similar variety, 'Pearl Skyblue', for comparison. As a result, it was concluded that this petunia plant is distinguishable from any other variety, whose existence is known to us, and this new variety of petunia plant was named 'Suntory SP-R'.

In the following description, the color-coding is in accordance with the Horticultural Color Chart of The Royal Horticultural Society, London, England (R.H.S. Color Chart), and the Inter-Society Color Council-Nation Bureau of Standards Color Name (I.S.C.C.-N.B.S. Color Name). A color chart based on The Japan Color Standard for Horticultural Plant (J.H.S. Color Chart) is also added for reference.

The female parent used in the breeding of 'Suntory SP-R' is a petunia plant having a reddish purple petal which was selected from a crossing of a wild type of petunia plant native to Brazil, the seeds of this was gathered at Gramado, Rio Grando Do Sul, Brazil and introduced to Japan in October, 1983. This wild type of plant is presently maintained at the aforementioned Plant Biotechnology Laboratory of Suntory Ltd. The main botanical characteristics of this female parent P105 are as follows.

Growth habit: Erect — Medium.

Plant height: 17 cm.

Spreading area of plant: The stem extends to a length of 12 cm from the base, and thus the spreading area of the plant is 20 cm in diameter.

Growth: Vigorous with abundant branching, profusion of bloom.

Blooming period: April to September, in all areas of Japan. The plant shape does not change throughtout this period.

Stem: Extending to 12 cm.

- *Thickness.*—1.6 mm.
- *Anthocyanin pigmentation.*—Absent.
- *Pubescence.*—Medium.
- *Branching.*—Few (primary), over-abundant (secondary), spreading by rooting at the base of stems.
- *Length of internode.*—17 mm.

Leaf:

- *Leaf attaching angle.*—Horizontal.
- *Shape.*—Lanceolate.
- *Length.*—3.5 cm.
- *Width.*—1.4 cm.
- *Color.*—Deep yellow green (J.H.S. No. 3707).
- *Pubescence.*—Few.
- *Petiole of main stem.*—Absent.

Flower:

- *Facing direction.*—Horizontal.
- *Type.*—Single.
- *Shape.*—Funnel-shape, with five-fissured limb.
- *Diameter.*—25 mm.
- *Color.*—Vivid reddish purple (R.H.S. No. 74A, J.H.S. No. 9207), bottom throat inside portion vivid greenish yellow (J.H.S. No. 2906), throat outside portion strong purplish pink (J.H.S. No. 8904).

*Reproductive organs.*—1 normal pistil and 5 normal stamens. Pistil is narrow shape and stamens are narrow shape.

*Peduncle.*—2.7 cm in length.

The pollen parent used in the breeding of 'Suntory SP-R' is a petunia plant having a reddish purple petal, different from the female parent, which was selected from a crossing of a wild type of petunia plant native to Brazil, the seeds of this were gathered at Gramado, Rio Grando Do Sul, Brazil and introduced to Japan in October, 1983. This wild type of plant is presently maintained at the aforementioned Plant Biotechnology Laboratory of Suntory Ltd. The main botanical characteristics of the male parent P107 are as follows.

Growth habit: Erect. The branches erect from the base of a stem.

Plant height: 17 cm.

Spreading area of plant: The stem extends to a length of 11 cm from the base, and thus the spreading area of the plant is 10 cm in diameter.

Growth: Vigorous with abundant branching, profusion of bloom.

Blooming period: April to September, in all areas of Japan. The plant shape does not change throughout this period.

Stem: Extending to 11 cm.

*Thickness.*—1.6 mm.

*Anthocyanin pigmentation.*—Absent.

*Pubescence.*—Medium.

*Branching.*—Few (primary), over-abundant (secondary), spreading by rooting at the base of stems.

*Length of internode.*—15 mm.

Leaf:

*Leaf attaching angle.*—Horizontal.

*Shape.*—Lanceolate.

*Length.*3.2 cm.

*Width.*1.3 cm.

*Petiole of main stem.*—Absent.

*Color.*—Deep yellow green (J.H.S. No. 3707).

*Pubescence.*—Few.

Flower:

*Facing direction.*—Horizontal.

*Type.*—Single.

*Shape.*—Funnel-shape, with five-fissured limb.

*Diameter.*—27 mm.

*Color.*—Vivid reddish purple (R.H.S. No. 74A, J.H.S. No. 9207), bottom throat inside portion vivid greenish yellow (J.H.S. No. 2906), throat outside portion strong reddish purple (R.H.S. No. 72C, J.H.S. No. 8905).

*Reproductive organs.*—1 normal pistil and 5 normal stamens. Pistil is narrow shape and stamens are narrow shape.

*Peduncle.*1.8 cm in length.

This new and distinct variety of petunia plant, 'Suntory SP-R', was asexually reproduced by cutting at the aforementioned Plant Biotechnology Laboratory, Institute for Fundamental Research of SUNTORY Ltd., residing at 2913-1 Torihara, Hakushu-cho, Kitakoma-gun, Yamanashi-ken, Japan, and the homogeneity and stability thereof were confirmed.

SUMMARY OF THE VARIETY

The new variety of petunia plant has an intermediate growth habit between upright habit and decumbent habit, which is almost similar to 'Pearl Skyblue'. The plant has a great profusion of flowers with a very small diameter, and very small stem thickness, which are much smaller than these of the similar variety, 'Pearl Skyblue'. The length of internode of the new variety is longer than that of 'Pearl Skyblue'. The flowers of the new variety are single, and very small, the petal has a vivid reddish purple color, and the bottom throat inside portion of the corolla has a vivid greenish yellow color, which are distinguishable from the similar variety, 'Pearl Skyblue'.

The plant is highly resistant to rain, heat, cold, and diseases.

DESCRIPTION OF THE VARIETY

Figure 1:
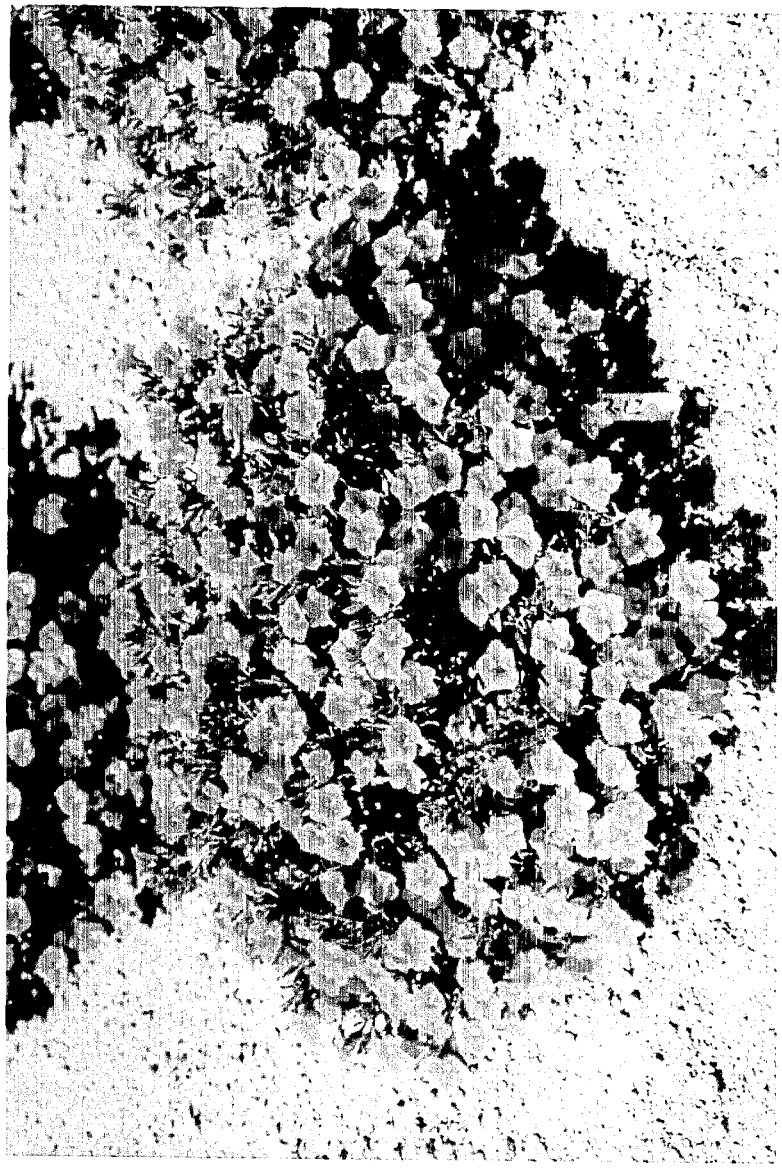
FIG. 1 is a photograph giving a partial view of the new variety of petunia plant planted in a flower bed.
Figure 2:
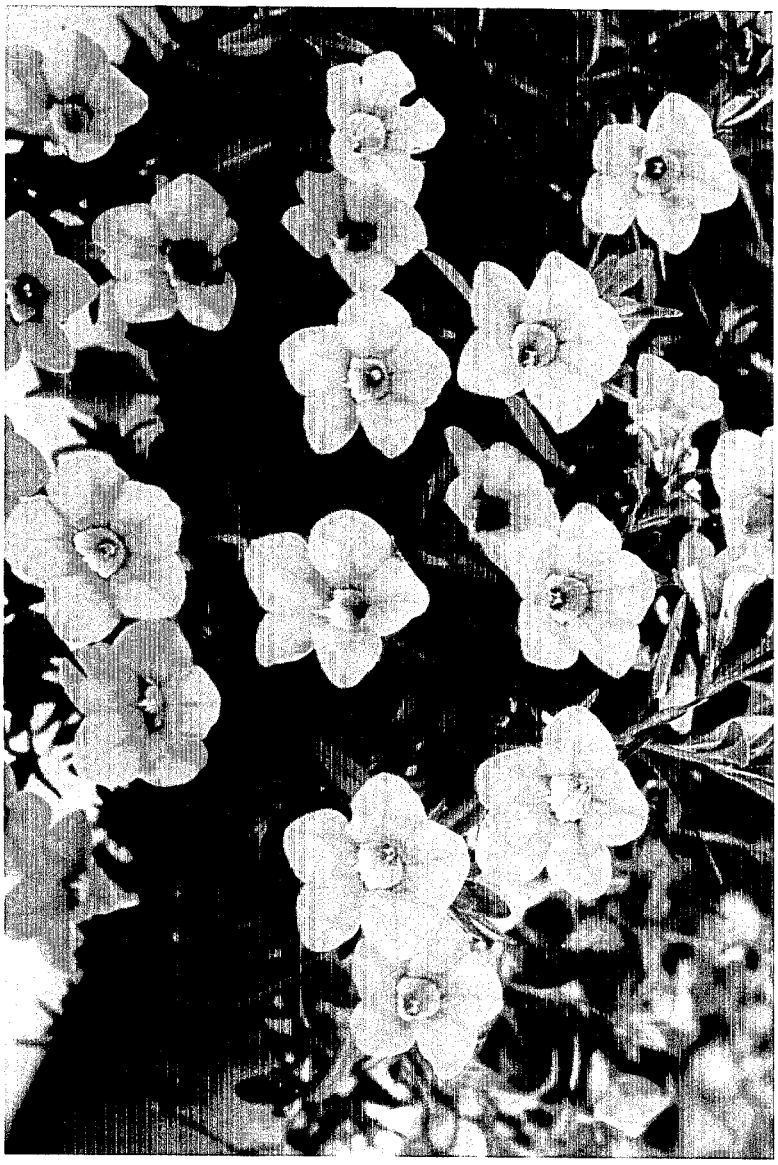
FIG. 2 is photograph of flowers of the new variety of petunia plant.
Figure 3:
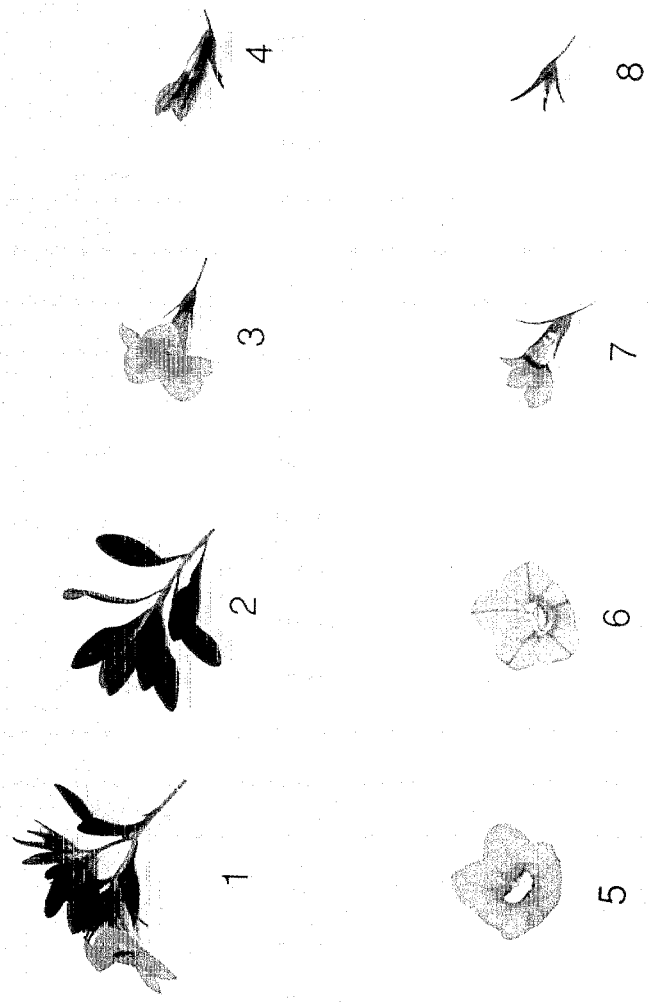
FIG. 3 is a photograph showing, in numerical order, a flower cluster (1), a current shoot (2), a flower (3), a bud (4), a front view of a petal (5), a rear view of a petal (6), a cross-sectional view of the flower (7), and pistil and stamens (8)
Figure 4:
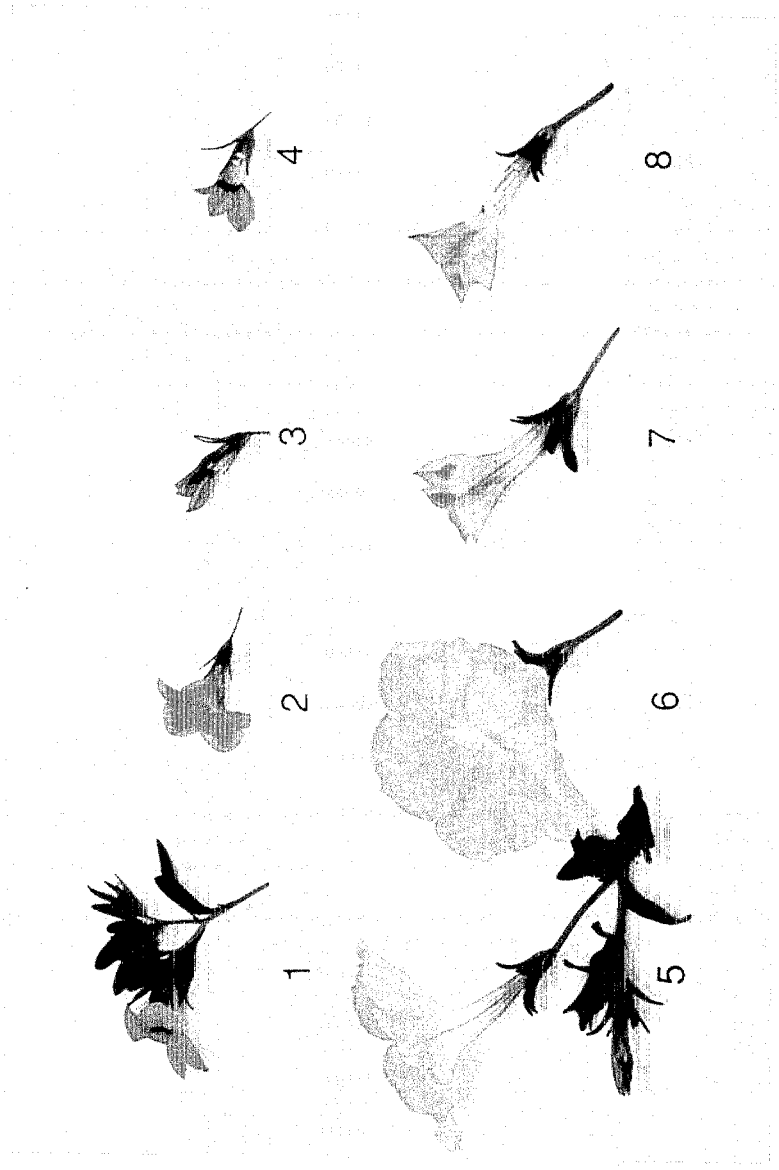
FIG. 4 is a photograph showing, in numerical order, a flower cluster (1), a flower (2), a bud (3), and a cross-sectional view of the flower (4) of the new variety of petunia plant, in comparison with corresponding items (5 to 8) of a similar variety 'Pearl Pink'.

The botanical characteristics of the new and distinct variety of petunia plant 'Suntory SP-R' are as follows.

Plant:

*Growth habit.*—Intermediate. The branches spread from the base of a stem obliquely upward.

*Plant height.*—20 cm.

*Spreading area of plant.*—The stem extends to a length of 10 cm from the base, and thus the spreading area of the plant is 30 cm in diameter.

*Growth.*—Very vigorous with abundant branching, a great profusion of bloom; the whole bush remaining in bloom for a considerable period of time.

*Blooming period.*—Late March to the beginning of October, in all areas of Japan. The plant shape does not change throughout this period.

Stem: Extending to 10 cm.

*Thickness.*—1.5 mm.

*Anthocyanin pigmentation.*—Absent.

*Pubescence.*—Medium.

*Branching.*—Medium (primary), over-abundant (secondary), spreading by rooting at the base of stems.

*Length of internode.*—17 mm.

Leaf:

*Leaf attaching angle.*—Horizontal.

*Shape.*—Lanceolate.

*Length.*—3.5 cm.

*Width.*—1.5 cm.

*Petiole of main stem.*—Absent.

*Color.*'Deep yellow green (J.H.S. No. 3707).

*Pubescence.*—Few.

Flower:

*Facing direction.*—Horizontal.

*Type.*—Single.

*Shape.*—Funnel-shape, with five-fissured limb.

*Diameter.*—25–30 mm.

*Color.*—Vivid reddish purple (R.H.S. No. 74A, J.H.S. No. 9207), bottom throat inside portion vivid greenish yellow J.H.S. No. 2906), throat outside portion light yellow green (R.H.S. No. 1C or 2D, J.H.S. No. 3103).

*Reproductive organs.*—1 normal pistil and 5 normal stamens (2 stamens are higher than pistil). Pistil is narrow shape and stamens are narrow shape.

*Peduncle.*—2.7 cm in length.

Physiological and ecological characteristics: High resistance to cold, rain, and heat. Moderate resistance to disease and pest.

This new variety of petunia plant is most suitable for flower bedding and potting, particularly in hanging pots or planters, and further excellent for ground cover.

The plant of this new variety 'Suntory SP-R' is presently planted and maintained at the Plant Biotechnology Laboratory, Institute for Fundamental Research of SUNTORY Ltd., residing at 2913-1 Torihara, Hakushu-cho, Kitakoma-gun, Yamanashi-ken, Japan.

We claim:

1. A new and distinct variety of petunia plant, substantially as herein illustrated and described, characterized particularly as to novelty by (A) an abundant branching and a great profusion of blooms, the whole bush remaining in bloom for a considerablle period of time, (B) flowers that are single and very small, the petals having a vivid reddish purple color and vivid greenish yellow throat inside portion, and (C) a high resistance to cold, rain, heat, and disease.

* * * * *